(12) United States Patent
Milesi et al.

(10) Patent No.: US 11,707,543 B2
(45) Date of Patent: Jul. 25, 2023

(54) SYSTEM FOR THE INTERNAL DISINFECTION OF CONTAINERS

(71) Applicant: SMI S.P.A., Bergamo (IT)

(72) Inventors: Giovanni Milesi, Bergamo (IT); Ivan Cortnovis, Bergamo (IT); Edgar Fischer, Bergamo (IT)

(73) Assignee: SMI S.P.A., Bergamo (IT)

( * ) Notice: Subject to any disclaimer, the term of this patent is extended or adjusted under 35 U.S.C. 154(b) by 383 days.

(21) Appl. No.: 16/906,774

(22) Filed: Jun. 19, 2020

(65) Prior Publication Data
US 2020/0397932 A1 Dec. 24, 2020

(30) Foreign Application Priority Data

Jun. 20, 2019 (IT) .................... 102019000009591

(51) Int. Cl.
| | |
|---|---|
| *A61L 2/10* | (2006.01) |
| *A61L 2/08* | (2006.01) |
| *A61L 2/24* | (2006.01) |
| *A61L 9/014* | (2006.01) |
| *B67C 3/22* | (2006.01) |
| *B67C 7/00* | (2006.01) |

(52) U.S. Cl.
CPC ................ *A61L 2/10* (2013.01); *A61L 2/084* (2013.01); *A61L 2/085* (2013.01); *A61L 2/24* (2013.01); *A61L 9/014* (2013.01); *B67C 3/22* (2013.01); *B67C 7/0006* (2013.01); *A61L 2202/11* (2013.01); *A61L 2202/18* (2013.01); *A61L 2202/23* (2013.01); *A61L 2209/14* (2013.01); *B67C 2003/227* (2013.01); *B67C 2007/006* (2013.01)

(58) Field of Classification Search
CPC . A61L 2/10; A61L 2/084; A61L 2/085; A61L 2/24; A61L 2202/11; A61L 2202/23
See application file for complete search history.

(56) References Cited

U.S. PATENT DOCUMENTS 9,889,216 B2 * 2/2018 Bellec ................. B29C 49/4252
2016/0257055 A1 * 9/2016 Hayakawa ................ A61L 2/06

FOREIGN PATENT DOCUMENTS

EP 2650252 A1 10/2013

OTHER PUBLICATIONS

Italian Search Report for priority Italian Patent Application No. IT2016000009591, dated Feb. 21, 2020, 10 pages.
"Definition and relationship to the electromagnetic spectrum", Wikipaedia Excerpt, 1 page.

* cited by examiner

*Primary Examiner* — Timothy C Cleveland
(74) *Attorney, Agent, or Firm* — Armstrong Teasdale LLP

(57) ABSTRACT

The present invention relates to a system for the disinfection of containers in a blowing and filling system of the containers with a product, in particular a system for the internal disinfection of the containers by means of ultraviolet-C radiation LED emitters.

12 Claims, 15 Drawing Sheets

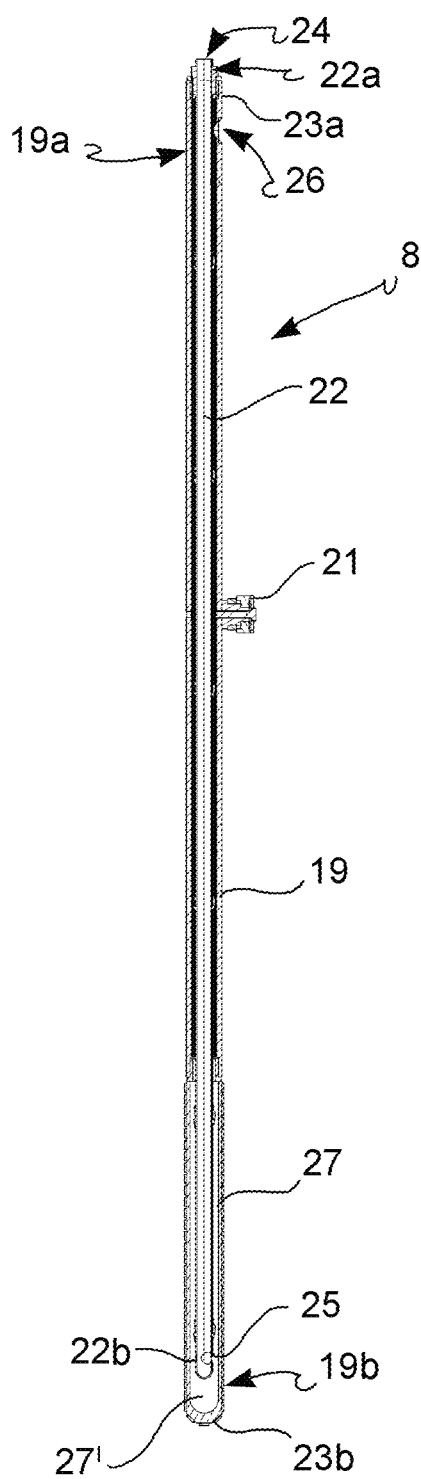
FIG. 5
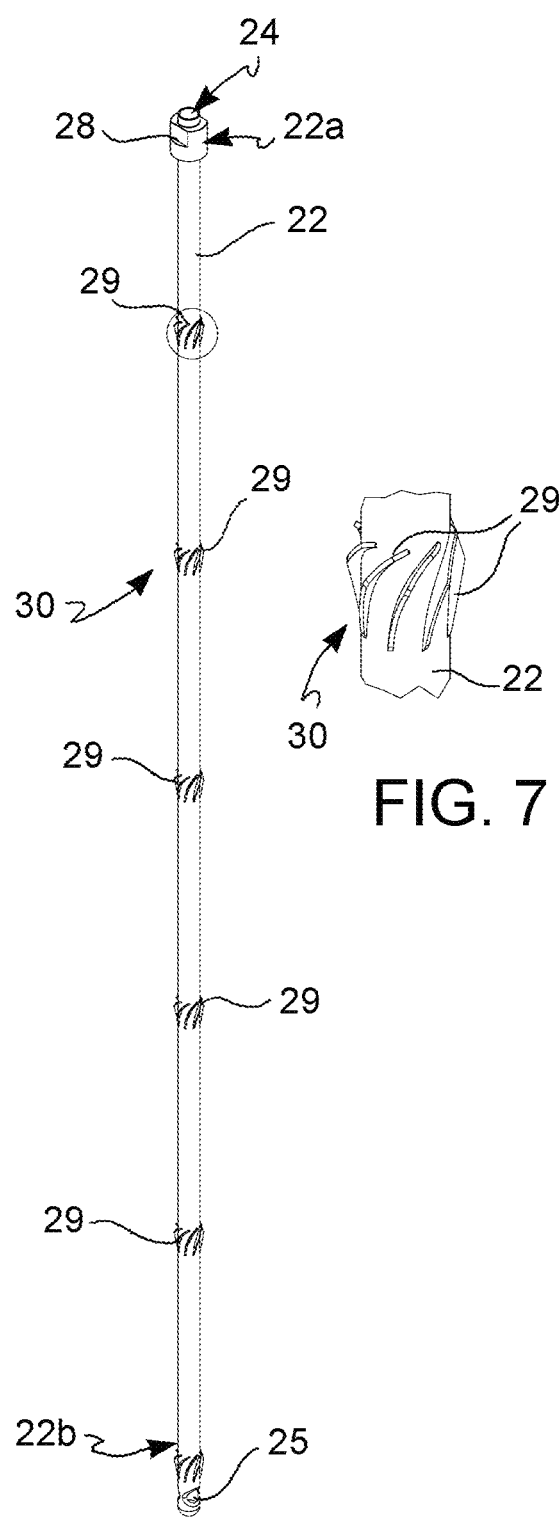
FIG. 7
FIG. 6

SYSTEM FOR THE INTERNAL DISINFECTION OF CONTAINERS

CROSS-REFERENCE TO RELATED APPLICATIONS

This application claims the benefit of priority to Italian Patent Application No. 102019000009591, filed on Jun. 20, 2019, the entire contents and disclosure of which are hereby incorporated by reference herein.

FIELD OF THE INVENTION

The present invention relates to a system for the disinfection of containers in a blowing and filling system of said containers with a product, in particular a system for the internal disinfection of said containers by means of ultraviolet-C radiation LED emitters.

BACKGROUND ART

As is known, filling containers with products which are sensitive to microbiological contamination (for example, milk and similar products) requires a hygienic level in the filling step defined as "ultra-clean", i.e. filling in class IV Standard VDMA 2/2000 3rd version 2016, and as "aseptic", i.e. filling in class V Standard VDMA 2/2000 3rd version 2016.

Currently, the main disinfection systems of containers require using oxidizing and germicidal substances which results in many drawbacks, such as:
  risk of residues of the germicidal treatment which may contaminate the food product;
  risk of contamination of the operator him/herself during the replenishment and handling step.

Other disinfection systems of containers are also known, all implicating various disadvantages, in particular:
  pulsed light which, due to the conformation of the electric-arc lamp, requires feeding at the two ends, and therefore it has an incompatible volume with the narrow neck of most bottles. The pulsed light further requires a significant electric power, to be provided in various consecutive pulses, and therefore requires the use of very powerful power supply systems. Finally, only about 20% of the pulsed light emission spectrum is in the germicidal electromagnetic radiation field, while the remaining 80% of the emission spectrum is not only ineffective, but, at given wavelengths, may activate damage repair mechanisms in the micro-organisms which risk nullifying the operation.
  low-pressure UV lamps which, although they have a spectrum which is concentrated in the range of effective wavelengths, emit a very modest quantity of energy, which therefore is insufficient for radiating the inside of a container in automated bottling machines. Further, these lamps use mercury vapors with timing for reaching operating speed and optimal operating temperatures which are not compatible with the use in automated bottling machines. Further, the use of mercury vapors is in contrast with the next European environmental standards.
  high-pressure UV lamps which, although they have a greater emission of energy, result in the same disadvantages as the low-pressure UV lamps and further involve a risk of explosion.

SUMMARY OF THE INVENTION

The problem at the basis of the present invention therefore is the one of providing a system for the disinfection of containers in a blowing and filling system of said containers with a product sensitive to microbiological contamination.

Such a problem is resolved by a blowing and filling system of containers with a product sensitive to microbiological contamination, said system comprising a disinfection unit as defined in the accompanying claims, which definitions form an integral part of the present description.

A first object of the invention therefore is a blowing and filling system of containers comprising a disinfection unit of the containers subjected to the blowing step, wherein said disinfection unit comprises a plurality of disinfection elements comprising germicidal UV-C radiation LED emitters.

A second object of the invention is a blowing and filling system of containers comprising a disinfection unit of the preforms as defined above, arranged upstream of the blowing station.

Further features and advantages of the present invention will become more apparent from the description of certain embodiments thereof, given hereinbelow only by way of a non-limiting, indicative example.

BRIEF DESCRIPTION OF THE DRAWINGS

FIG. 5 shows a side sectional view of the detail in FIG. 4;

FIG. 6 shows a perspective view of an inner element of the detail in FIG. 5;

FIG. 7 shows an enlarged perspective view of a portion of the element in FIG. 6;

DETAILED DESCRIPTION OF THE INVENTION

Figure 1:
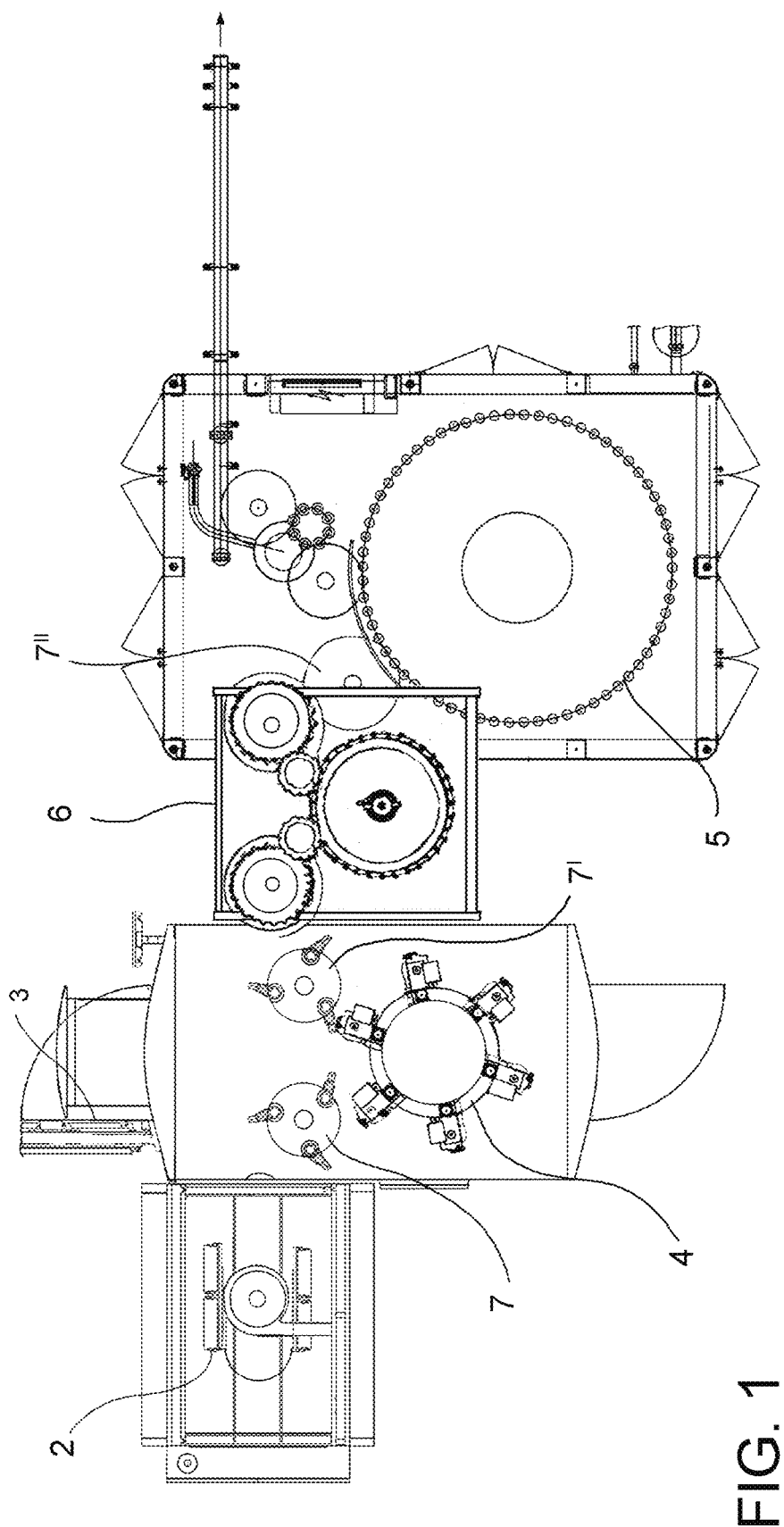
FIG. 1 shows a simplified plan view of a first embodiment of a blowing and filling system comprising a unit for the internal disinfection of containers in accordance with the invention.

With reference to the figures, a blowing and filling system of containers in accordance with the invention, which is indicated as a whole with numeral 1, comprises a heating oven 2 for preforms P inlet into the system by means of suitable handling means 3, a blowing unit 4 placed downstream of oven 2, a filling unit 5 with a filling product, arranged downstream of the blowing unit 4, and a disinfection unit 6 which, in the embodiment in FIG. 1, is arranged in intermediate position between the blowing unit 4 and the filling unit 5. In such an embodiment, therefore, the disinfection unit 6 is adapted to disinfect containers, conventionally bottles, outlet from the blowing unit 4.

The blowing unit 4 and the filling unit 5 preferably are of the rotary type and comprise suitable distribution stars 7, 7', 7" for handling the preforms and containers, respectively.

The blowing 4 and filling 5 units are of the conventional type and therefore are not described in greater detail. The blowing unit 4 preferably is a stretch-blowing unit.

Figure 8:
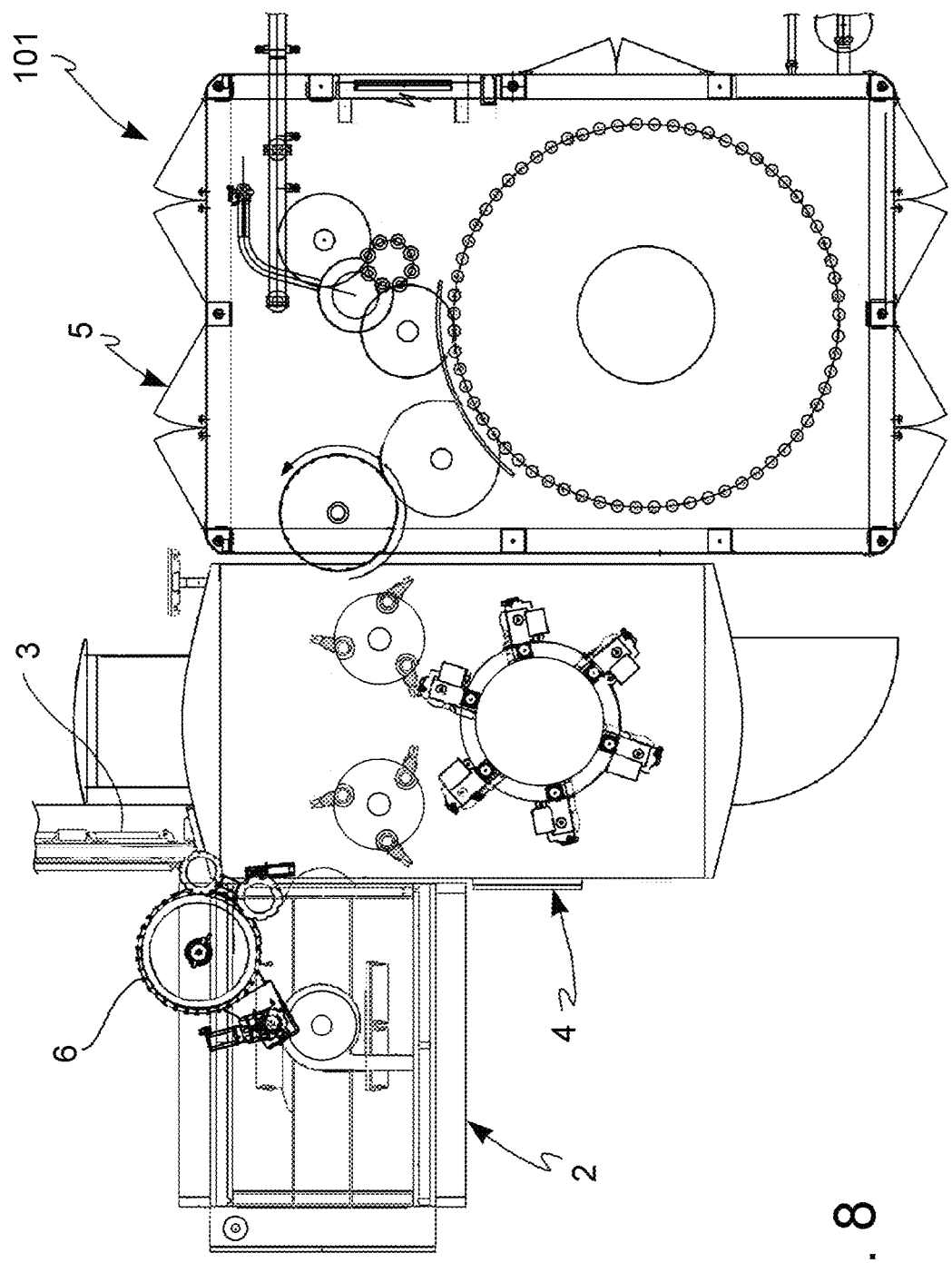
FIG. 8 shows a simplified plan view of a second embodiment of a blowing and filling system comprising a unit for the internal disinfection of containers in accordance with the invention.
Figure 9:
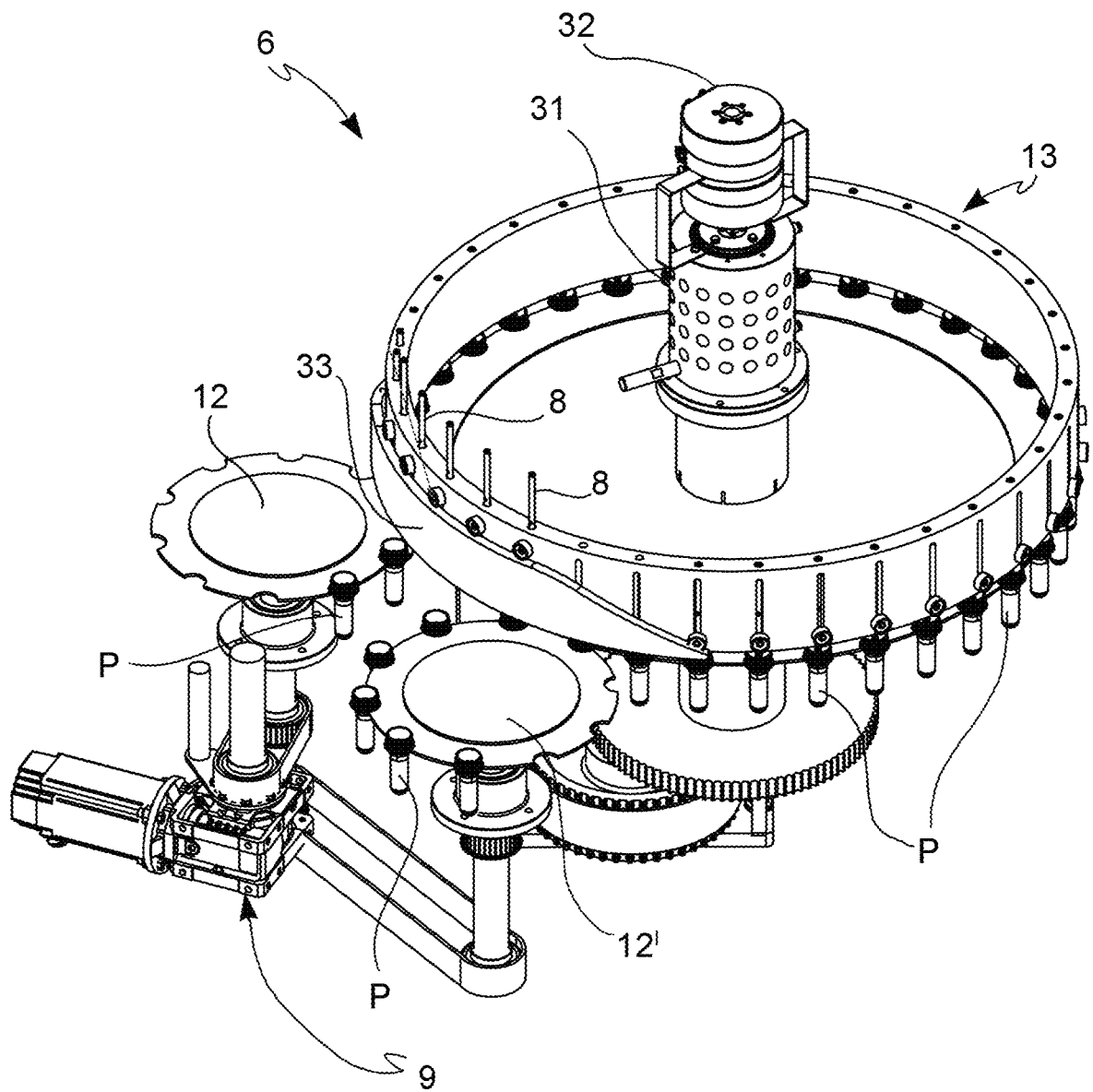
FIG. 9 shows a simplified perspective view of a unit for the internal disinfection of containers according to the embodiment in FIG. 8.
Figure 10A:
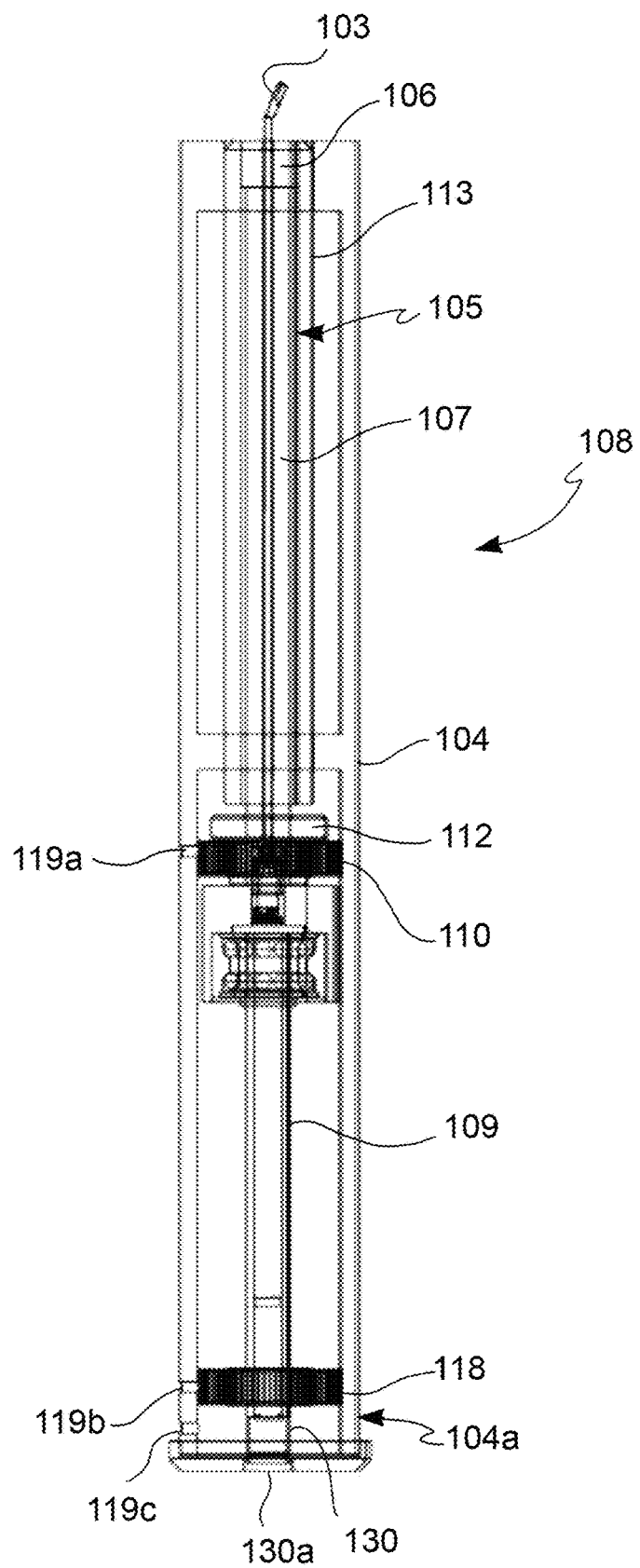
FIG. 10A shows a side sectional view of a disinfection member according to a different embodiment of the invention.
Figure 10B:
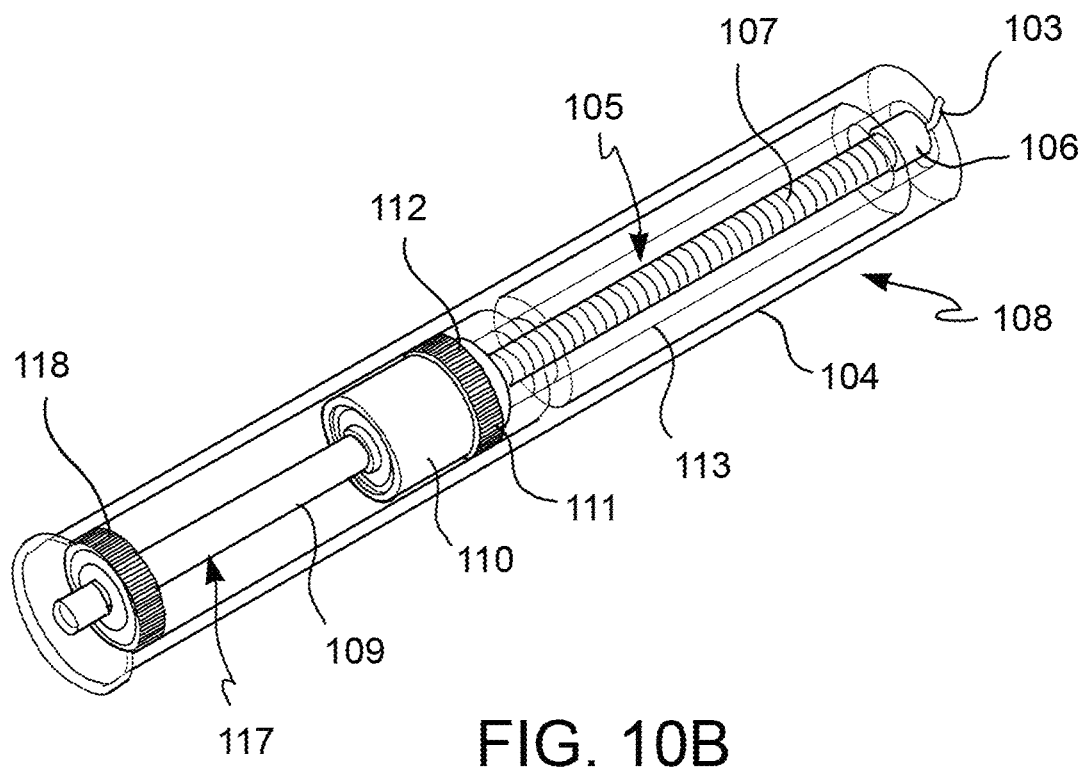
FIG. 10B shows a transparency perspective view of the disinfection member in FIG. 10A.
Figure 10C:
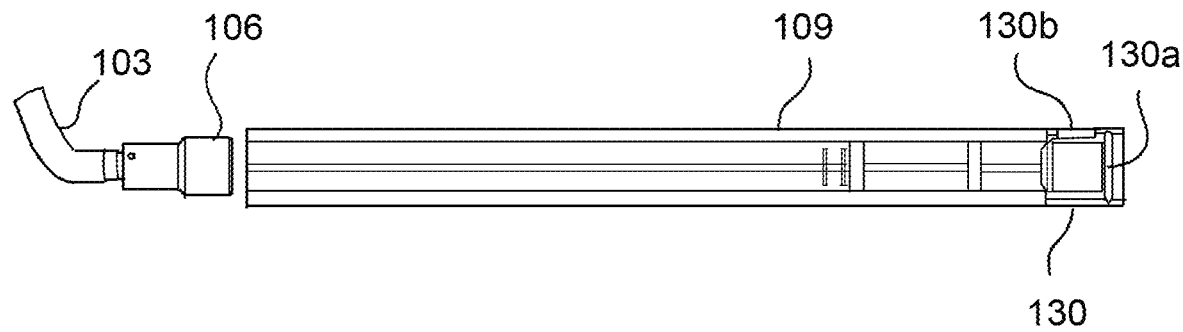
FIG. 10C shows a transparency side view of the disinfection member in FIG. 10A.

In a different embodiment shown in FIGS. 8 and 9, the blowing and filling system of containers, which is indicated as a whole with numeral 101, comprises a heating oven 2 for preforms P inlet into the system by means of suitable handling means 3, a blowing unit 4 placed downstream of oven 2, a filling unit 5 with a filling product, arranged downstream of the blowing unit 4, and a disinfection unit 6 which, as shown in FIG. 8, is arranged in intermediate position between the handling means 3 and oven 2. In such an embodiment therefore, the disinfection unit 6 is adapted to disinfect preforms P inlet into oven 2.

Figure 2:
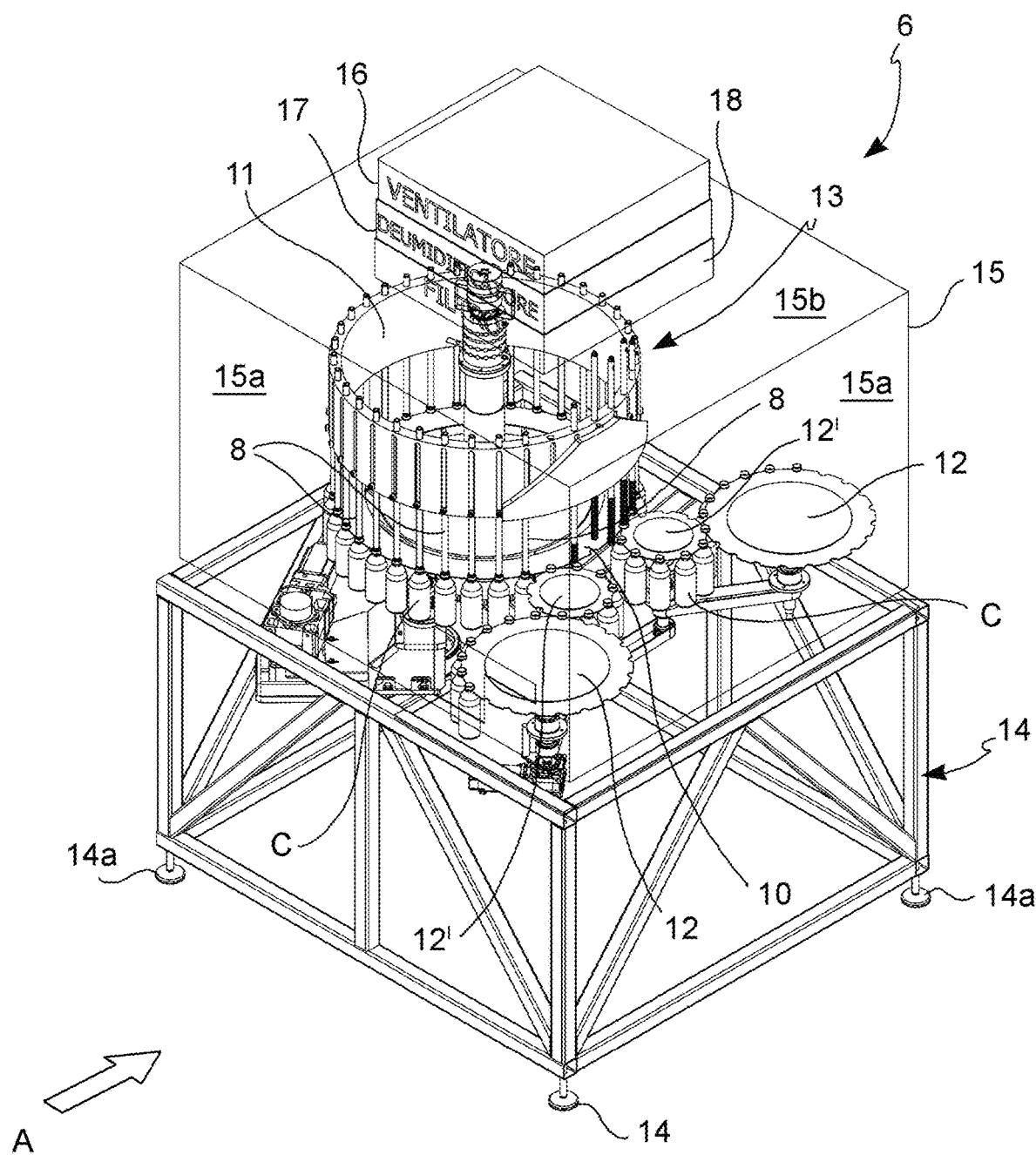
FIG. 2 shows a simplified perspective view of a unit for the internal disinfection of containers in accordance with the invention.
Figure 3:
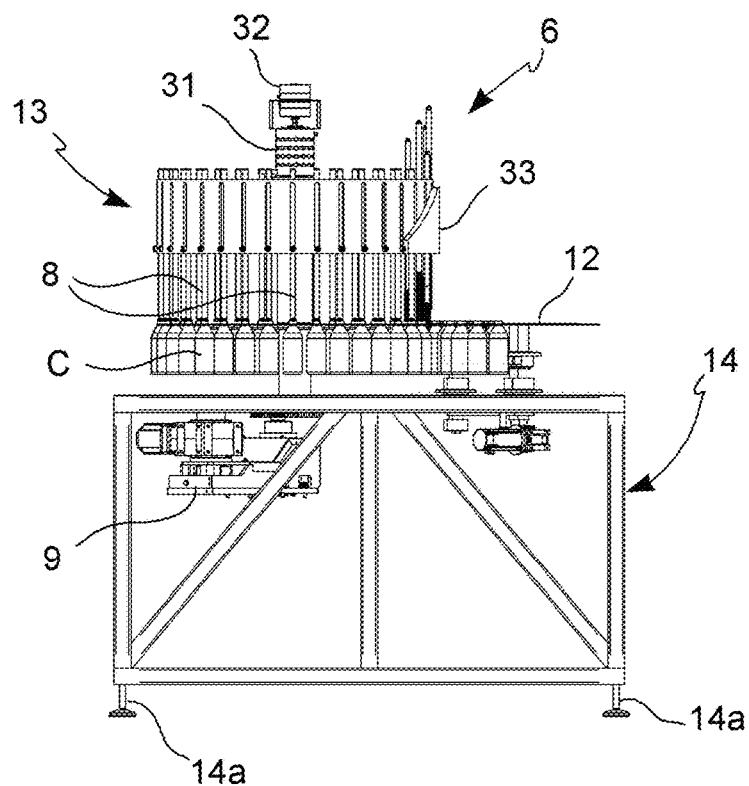
FIG. 3 shows a side view of the unit for the internal disinfection of containers according to direction A in FIG. 2.
Figure 4:
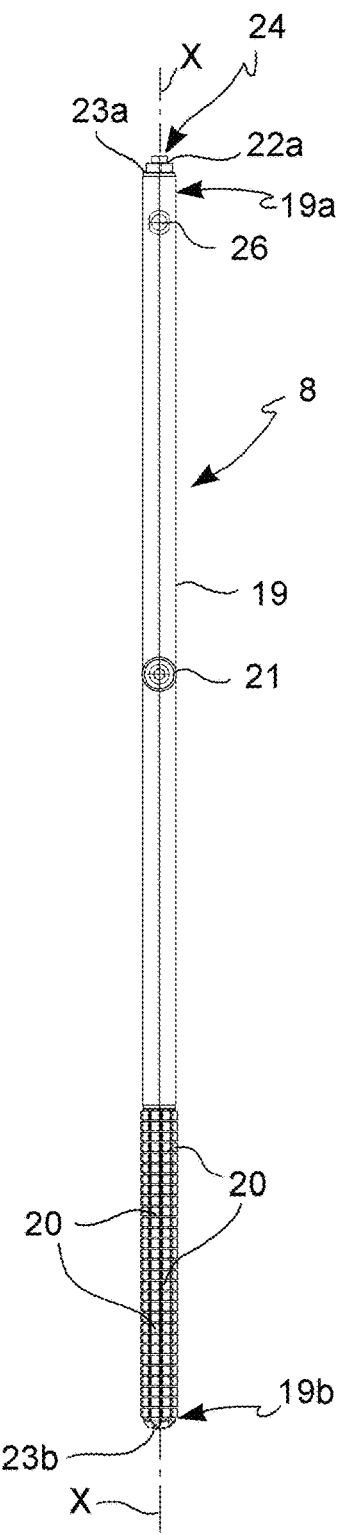
FIG. 4 shows a side view of a detail of the unit for the internal disinfection of containers in FIG. 3.

With reference to FIGS. 2, 3 and 9, the disinfection unit 6 of containers C or preforms P comprises a carousel 13 on which there is supported a plurality of disinfection members 8, which are movable between a raised position and a lowered position, wherein said lowered position is configured so as to allow the disinfection members 8 to be introduced into said containers C or preforms P to be disinfected.

Carousel 13 is moved in rotation by a suitable drive system 9 and comprises a support disc 10 on which periphery there is arranged a plurality of support elements for the neck of the containers C or preforms P, when these are picked and put into rotation by carousel 13. The support structure 11 of the disinfection members 8 is positioned above the support disc 10, which support structure 11—being fastened to carousel 13—is rotatable integrally with the support disc 10.

Suitable distribution stars 12, 12' are coupled tangent to one another with carousel 13 so as to feed carousel 13 with the inlet containers C or preforms P, and to pick the outlet disinfected preforms P or containers C so as to send them to the successive processing, which in the embodiment in FIG. 1, is the filling unit 5, while in the embodiment in FIG. 8, it is oven 2.

Carousel 13 and the distribution stars 12, 12' are supported on a frame 14 provided with legs 14*a* and are enclosed in a containment structure 15 in which a controlled atmosphere is maintained, conventionally by means of an overpressure of sterile air.

The containment structure 15 is configured to allow both the visual operating inspection, for example by means of suitable warning LEDs on each disinfection member 8, and an adequate protection for the operator from the ionizing radiation used for disinfecting. The containment structure 15 conventionally comprises side walls 15*a* and a roof 15*b*.

The disinfection unit 6 further comprises ventilation means 16, downstream of which a dehumidification device 17 and a sterile filter 18 are arranged so as to introduce dry and sterile air into the containment structure 15. The air introduced preferably is pre-cooled air. The ventilation means 16, dehumidification device 17 and sterile filter 18 are arranged, for example on the roof of the containment structure 15.

With reference to FIGS. 4 to 7, according to an embodiment, the disinfection members 8 comprise a tubular body 19 which extends along an axis X-X and which preferably has a homogeneous diameter which is smaller than the opening of the neck of container C or preform P so as to be inserted therein without interference.

The tubular body 19 is configured for a refrigerant fluid, preferably chilled water, to flow therein.

The tubular body 19 has a proximal portion 19*a* and a distal portion 19*b*, the latter being configured to be inserted into container C or preform P through the neck opening. The proximal portion 19*a* is open at the proximal end 23*a* thereof, while the distal portion 19*b* is closed at the distal end 23*b* thereof.

The distal portion 19*b* of the tubular body 19 comprises a plurality of UV-radiation disinfection elements 20 on the outer surface thereof. The disinfection elements 20 preferably cover both the cylindrical part of the distal portion 19*b* and the (preferably hemispherical) surface of the distal end 23*b*.

The disinfection elements 20 preferably are UV-C radiation LEDs, characterized by a narrow emission spectrum in the 200-290 nm range, with peak wavelengths preferably of 265 nm and/or 275 nm. These features ensure obtaining the maximum germicidal effect, while at the same time minimizing the energy dispersion at ineffective wavelengths for such a treatment.

The tubular body 19 also comprises an opening 26 arranged on the cylindrical surface of the proximal portion 19*a*, close to the proximal end 23*a*.

On the tubular body 19 there is further arranged a drive wheel 21, intended to interact with a cam 33 (shown in FIG. 3) to raise (member 8 not inserted in container C or preform P) and lower (member 8 inserted in container C or preform P) the disinfection members 8 during the operating steps of the machine.

The tubular body 19 houses therein a tube 22 which extends along axis X-X between a proximal end 22*a* and a distal end 22*b*.

The proximal end 22*a* of tube 22 protrudes externally with respect to the proximal end 23*a* of the tubular body 19 and ends with an opening 24. A second opening 25 is arranged proximal to the distal end 22b of tube 22, preferably on the cylindrical portion thereof adjacent to said extremity 22b.

The proximal end 22a of tube 22 further comprises connection means 28 to a pipe (not shown).

The outer diameter of tube 22 is less than the inner passage of the tubular body 19 so as to leave a gap 27 between the respective opposed surfaces. For the same reason, tube 22 has an extension along axis X-X which is less than the one of the tubular body 19 so as to create a space 27' between the respective distal ends 22b, 23b.

Opening 26 of the tubular body 19 is configured to introduce said refrigerant fluid, conventionally chilled water, which circulates in the annular gap 27 and in space 27' between tube 22 and the inner surface of the tubular body 19, as shown in FIG. 5, and then enters tube 22 through opening 25 to then leave opening 24 and, by means of said pipe, be collected by a return collector 31.

All tubes 22 of the disinfection unit 6 are connected to the return collector 31 (FIG. 3) of the refrigerant fluid by means of related fastening means 28 and suitable pipe.

Tube 22 comprises a plurality of ribs 29 along the outer surface thereof. The ribs 29 preferably have a shape of curved fins arranged along a circumference of tube 22 to form a crown 30. A plurality of crowns 30 is arranged, preferably at regular intervals, along axis X-X on the surface of tube 22.

The ribs 29 induce an adequate turbulence and mixing of the refrigerant fluid, which promotes the heat exchange with the surface of the tubular body 19 so as to effectively remove the heat generated by the disinfection elements 20.

In preferred embodiments, the cooling liquid comes from the cooling circuit already available in the blowing unit 4.

The disinfection unit 6 further comprises an electric collector 32 which distributes the electric energy to the LEDs of the disinfection members 8.

The advantages of the invention are easily deduced from the above, and in particular relate to the disinfection elements being capable of emitting only germicidal (narrow spectrum) radiation, operating at low power and being ecologically acceptable, not comprising mercury vapors.

In particular, the embodiment in FIG. 1 has the following advantages:
- it carries out the sterilization in the immediate vicinity of the filling machine, allowing a control over the excessive contamination, and therefore ensuring the system has good reliability of the overall process, eliminating the risk of contamination following the sterilization;
- it carries out the sterilization with UV-C radiation on the inner surface of the bottle after it was obtained by stretch-blowing from a preform P, which results in a tenfold decrease of the contamination per surface unit with respect to the preform, with reduction by equal factor of the radiating power required for the sterilization;
- the sterile and dry air introduced into the disinfection unit 6 makes the micro-organisms less resistant;
- the pre-heating of preform P and the dry high-pressure air flow used in the preceding steps promote the sterilization of the bottles.

The embodiment in FIG. 8, wherein the disinfection unit 6 is arranged upstream of oven 2, has the advantage of being a much more compact and affordable system because the pitch of the preforms is about 45 mm, rather than about 120 mm provided for bottles.

Alternative embodiments are shown in FIGS. 10A to 10D, 11A to 11B, 12, 13, 14, 15A to 15B and 16 to 19. Also in this case, the disinfection unit (not shown as a whole) is entirely similar to the above-described unit 6 and is arranged in the same position upstream of the filler in an ambient conditioned with filtered air.

Figure 11A:
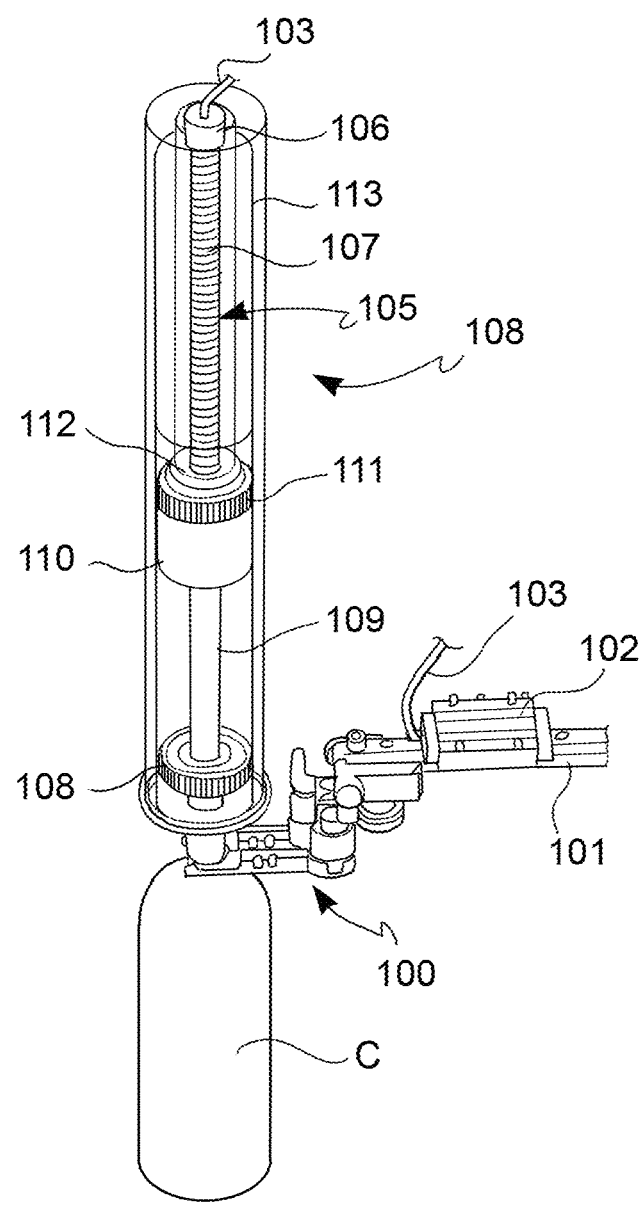
FIG. 11A shows a transparency perspective view of the disinfection unit comprising the disinfection member in FIG. 10A.
Figure 11B:
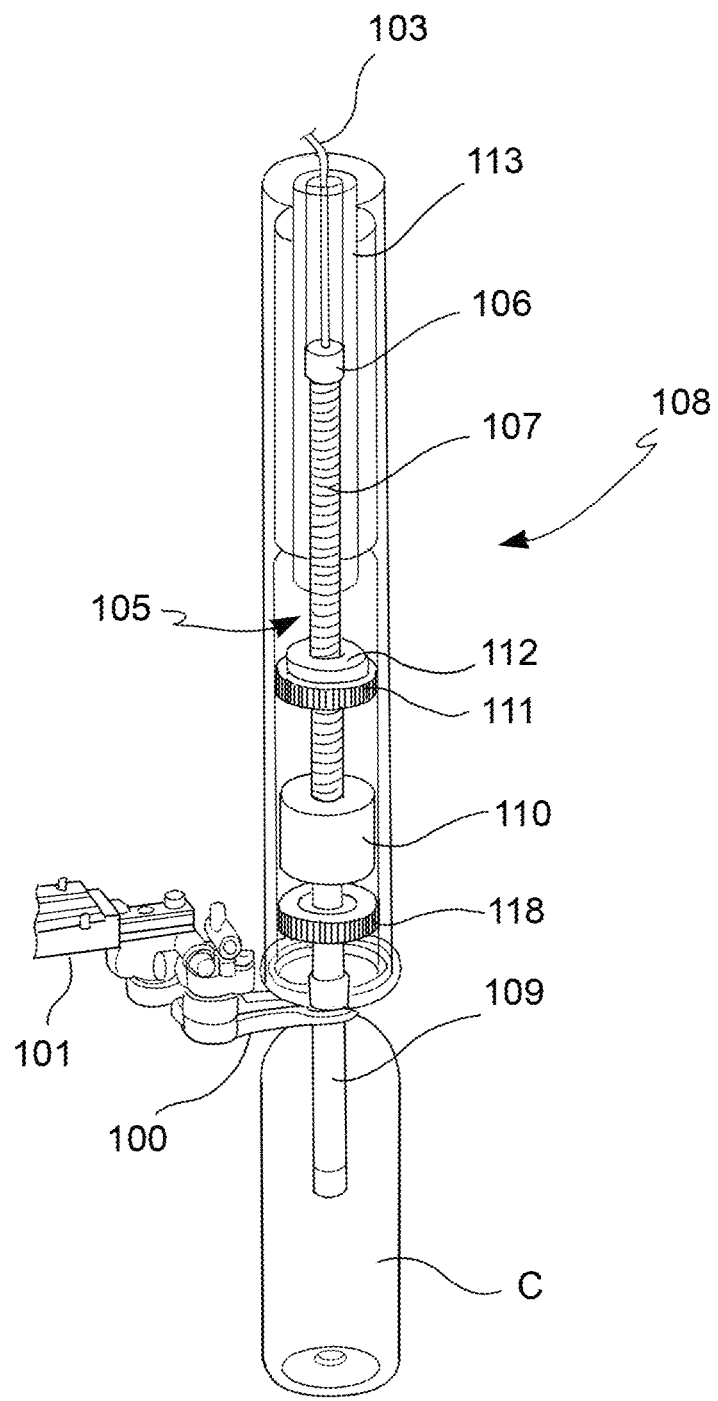
FIG. 11B shows a transparency perspective view of the disinfection unit in FIG. 11A, in a different operating condition.

In such embodiments, as shown in FIGS. 11A and 11B, bottle C is supported by its neck by a gripper 100 operatively fastened on an arm 101 associated with the carousel (not shown) of the disinfection unit 6. A disinfection member 108 is arranged above bottle C and aligned with the axis thereof. As described previously, the carousel of the disinfection unit 6 comprises a plurality of disinfection members 108, each operatively associated with a gripper 100 which supports a bottle C.

A laser source 102 is also fastened on or close to arm 101, the laser source being connected to the disinfection member 108 by means of flexible optical fiber 103.

In certain embodiments, there may be one laser source 102 for all the disinfection members 108 and it may be arranged in fixed position to the side of the carousel, in the mechanical and spatially most favorable position. Here, the laser source is coupled to the individual disinfection members by means of an electric and digital rotating collector, for example selected between those available on the market.

In other embodiments, the laser source 102 may be arranged directly above each disinfection member 108 so as to simplify the optical path and eliminate the need to transmit via optical fiber.

By using a dedicated laser source 102 for each bottle C being treated, the germicidal optical power may be varied in very short times to modulate the irradiance depending on the exposure of the surfaces lit at that moment, and thereby all the adjusting is left only to the modulation of the laser source. The laser source, conventionally a diode laser, may emit a collimated beam which directly pushes on the optical assembly of the disinfection member (see the description below) without further optical corrections.

The present invention provides employing germicidal UV-C radiation (250 to 330 nm) or visible-infrared radiation (VIR) (400-1200 nm) generated by laser source and introduced into the bottles in collimated form. The action of the radiation has the power to deactivate the micro-organism by means of the UV-C ionizing radiation which degrade the DNA, or by means of thermal effect with beams in the visible (400-700 nm) and/or infrared range (700-1200 nm) (VIR) which bring the micro-organisms to high temperatures such as to cause the pyrolysis of the organic matter and the irreversible damage thereof. The selection of one of the two types of radiation, UV or visible-infrared (VIR), is dictated by the following considerations: UV is more effective also at low powers, but it is not an easy radiation to generate and use on wave guides (optical paths). VIR radiation instead requires higher power than UV radiation, however if the wavelength is suitably selected, this radiation may be very effective. For example, if a wavelength is considered of about 940 nm, in general between 750 and 1100 nm, the PET, also colored and recycled, has a high transparency and therefore this radiation may operate with increased power, being mainly absorbed by the micro-organisms up to bringing them to temperatures which cause irreversible damage in very short times, in the order of one second, without degrading the PET. Given that the wavelengths are towards the infrared range, i.e. beyond 700 nm, the optical behavior of the PET intended as reflection, absorption and transmittance, is invariant with respect to the conventional coloring of the resin for bottles. Also concerning bottles loaded with materials that abate the transmission of radiation, such as for example, titanium dioxide and zinc oxide, a possible overheating of the PET would not result in aesthetical damage because the coloring caused by the oxide completely masks the possible aesthetical damage of the PET itself. From a technological viewpoint, the availability of laser sources at these wavelengths is vast, with high energy efficiency and moreover, the optical devices for this wavelength required to create an optical path are widely available on an industrial level.

The advantage of using a monochromatic source such as the LASER with respect to another source lies in the possibility of concentrating high power in well-delimited areas, the shape of the container being easily accommodated. As described below, the laser radiation may be guided into the bottle reaching—with values which can be determined and selected—each inner surface of the bottle, and it may be configured as a "blade of light" with increased intensity over a limited surface such as to degrade the micro-organism and leave unaltered the PET support by virtue of the rapidity of the action.

The laser source 102 may be cooled by water or electrically by means of a Peltier cooler, or Peltier cell, depending on the power of the laser source.

Figure 10D:
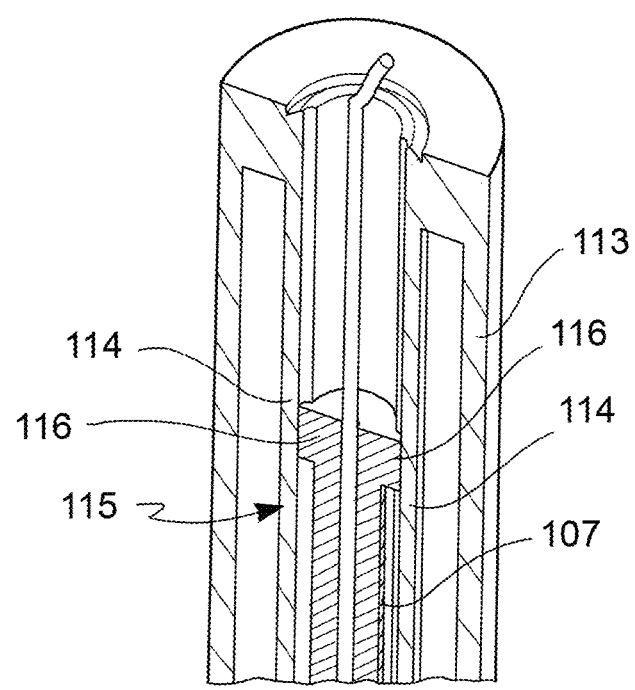
FIG. 10D shows a perspective view of a cut-away section of a detail of the disinfection member in FIG. 10A.

As shown in FIG. 10D, the disinfection member 108 comprises a casing 104 wherein a stem 105 is arranged, the stem being vertically movable between a raised position, in which the stem is positioned above the neck of bottle C, and a lowered position, in which the lower portion 109 of the stem is inserted in bottle C.

The optical fiber 103 is connected to a collimator 106, which serves the purpose of diffusing the radiation which crosses the fiber according to a light beam with a cylindrical section. The collimator is integral with stem 105 in the vertical translational motion.

Stem 105 comprises:
- an upper portion 107 having tubular shape, so as to incorporate therein the path of the optical fiber which transports the laser radiation, and with a feed-screw outer surface,
- a rotatable lower portion 109, containing therein a series of optical devices to conform the cylindrical radiation beam produced by the collimator 106 in a beam with a strongly thinned rectangular section and
- a bushing or bearing element 110 which is integral with the upper portion 107 and wherein the lower portion 109 is pivotally associated so as to maintain a low axiality tolerance with the screw containing the illuminator.

A first direct drive actuator 111, which is fastened to the inner wall of casing 104 in substantially median position (ensuring a correct axiality for the moving devices and excluding the need to feed the actuator with mobile cables), puts a guide element 112 (for example, a recirculating-ball guide, a screw or a helical guide made of self-lubricating material) into rotation, which guide element 112 applies a torque to the feed-screw surface of the upper portion 107. The upper portion 107 is inserted into a tubular element 113 comprising the vertical grooves 114. Shoes 116, which are inserted into said vertical grooves 114 so that the rotation of the upper portion 107 is prevented, are arranged at the upper end 115 of the upper portion 107. Therefore, the upper portion 107 may only take on a vertical translational motion under the action of the force applied by the first actuator 111, by virtue of the feed-screw profile which interacts with the rotating guide element 112. FIG. 11B shows an operating condition wherein stem 105 is in lowered position and is introduced into bottle C.

A second direct drive actuator 118 is positioned at the lower portion 109 of stem 105 and incorporates, in the rotor thereof, stem 105 itself. The rotary action is transmitted to the lower portion 109 of stem 105 by means of projections or shoes (not shown) associated with the rotor and which are inserted into longitudinal grooves 117 on said lower portion 109. The lower portion 109 of stem 105 therefore is free to slide vertically integrally with the translational motion of the upper portion 107 and rotates integrally with the rotor of the second actuator 118.

The actuators 111, 118 are direct drive actuators and the rotary motion thereof is transmitted by means of a coupling directly in the rotor thereof. On the market, these motors are defined as Direct Drive Rotary Servomotors, DC motors or STEP motors. This solution allows a rigid, compact and closed structure without resorting to using drive members, also due to the fact that the loads are very limited. Again due to the fact that the dynamic loads are very limited, the motors have a very low power and torque, and therefore they are not such as to require a forced cooling with fluid. The solution shown provides good compactness and especially an axial rigidity, which is highly beneficial for optimizing the shape of the optical beams; indeed the axiality tolerance between collimator 106 and the optical devices downstream is easily containable at acceptable values with this constructional solution.

Casing 104 comprises a first opening 119a and a second opening 119b at the first and second actuator 111, 118, respectively, to allow the wiring (power and signal connection), and a third opening 119c at the lower end 104a thereof, for the inlet of filtered compressed air for keeping the optical components on the end of the stem clean.

The embodiment shown above has the advantage of quickly adapting to a variation in size of the bottle by simply varying the parameters of the motor control, i.e. it allows a bottle format change only through digital parameters. In the embodiments described below, wherein the related motion is partly or totally left to the bottle, certain operations for mechanically adapting the machine may be required in the event of format change.

In a different embodiment indeed, the movement of stem 105 may be actuated by means of cam 33 (FIGS. 3 and 9) arranged along the curvilinear path of the carousel. The rotation of the lower portion 109 of stem 105 may be obtained in three ways:

a) stem 105 is put into rotation with a dedicated electronically-controlled motor (actuator 118), or b) stem 105 is put into rotation by means of a drive which transfers the rotation of the carousel to the optical assembly, for example by means of a rack system or by means of a screw which transforms the vertical motion given by the cam (or motor) into rotary motion, or c) the bottle is put into rotation, while stem 105 only has a vertical movement.

A further embodiment consists in keeping fixed the complete optical system and carrying out the vertical and rotary motion only by means of the movement of bottle C, which is raised and rotated again by means of dedicated electronically-controlled motors or by means of cam and drive from the motion of the carousel. The rotary and translational movements may be according to a fixed law.

According to other embodiments not specifically shown, stem 105 may be mounted in a vertically mobile support, for example sliding on a specific track, carried out by a drive system or a cam, and may be put into rotation by means of a specific drive system or by means of gear meshing and motion reduction which takes advantage of the drive system of the carousel.

As mentioned, stem 105 encloses therein an optical system 120 which defines the optical path of the radiation generated by the laser source 102 and which is described later with reference to FIGS. 12, 13, 14A to 14B, 15 and 16.

The optical system 120 comprises, in order:
a collimator 106;
a first and a second group of cylindrical micro-lenses 121, 122;
a first and a second cylindrical lens 123, 124;
an optical assembly 125 comprising, in order: i) a first concave cylindrical lens 126, ii) a beam splitter 127, iii) a second concave cylindrical lens 128 and iv) an optical wedge 129 arranged at the beam splitter, perpendicularly with respect to the first and second concave cylindrical lens 126, 128.

The beam splitter 127 is a very common optical device in optics and consists of two prisms 127a, 127b joined along a tilted plane 127c, here tilted by 45°. Prior to being joined, the two faces of the prisms 127a 127b are coated with a coating which allows the radiation to be divided into proportions which can be selected between lateral direction (beam F3, bottle wall) and longitudinal direction (beam F4, bottle bottom). When such a coating is a layer consisting of a photonic crystal, the related intensity of the two divisions of the two radiation beams may be selected during the disinfection process through an electrical or magnetic signal.

Figure 12:
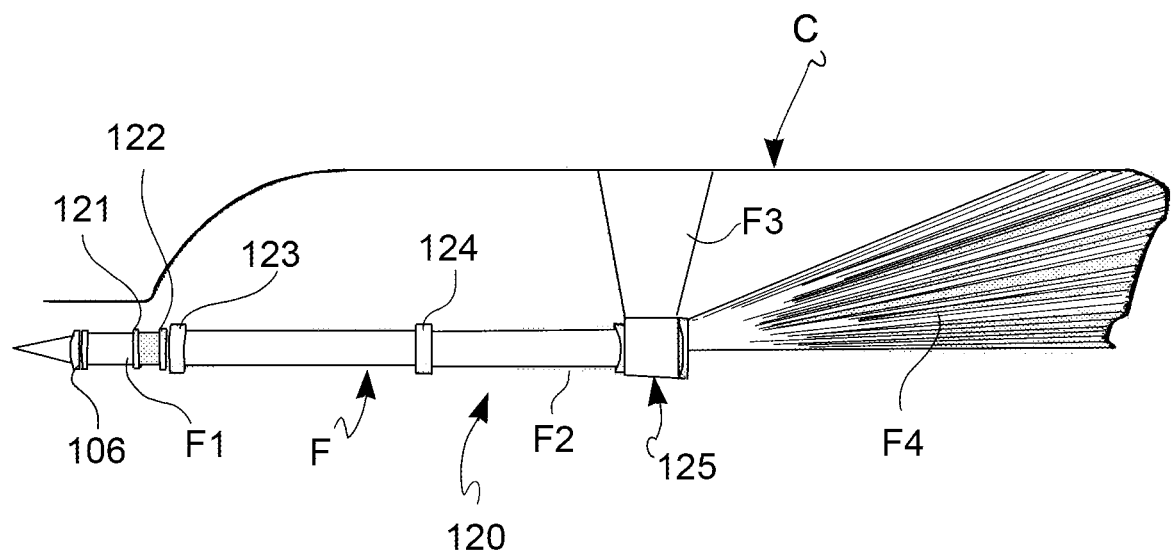
FIG. 12 shows a simplified diagrammatic side view of the disinfection member in FIG. 10A, in an operating condition.

Once outlet from the optical fiber, the modeling of the radiation beam F is the following. The assembly of optical devices is shown in FIG. 12.

The object of collimator 106 is to make the beams originating from the optical fiber 103 parallel and which form the radiation cylinder F1 that branches off from collimator 106 towards stem 105. The optical fiber 103 is suitably sized to have the correct opening of the radiation according to a conical geometry. The radiation impinges on the optical assembly of collimator 106 and a beam leaves therefrom overall with a cylindrical section with an increased degree of homogeneity concerning the intensity of the radiation according to the various orthogonal sections.

The cylindrical beam F1 travels the entire stem 105 which is hollow, and intercepts a first 121 and a second group 122 of cylindrical micro-lenses at a determined distance which is compatible with the maximum size of the bottles. These cylindrical lenses create an intermediate focal point wherein various micro-beams are created which then intercept a first cylindrical lens 123 (for example, a Fourier transform lens), and a second cylindrical lens 124 (for example, an orthogonal focusing lens), thus operating in suitable positions. Thus, a beam F2 in the manner of a blade is created, i.e. having very thin rectangular section with two very small sides.

Figure 14A:
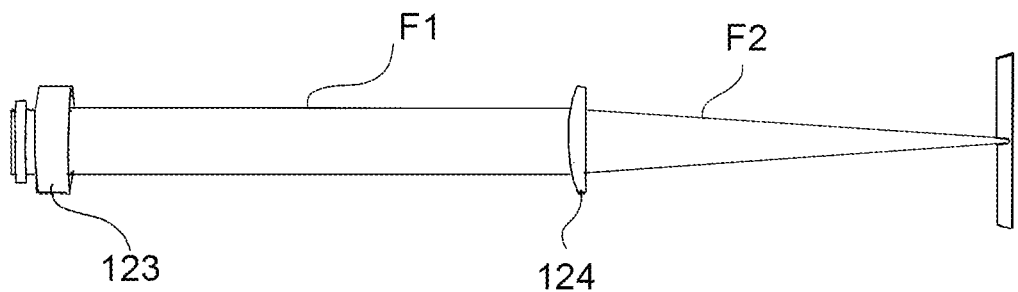
FIGS. 14A to 14B show a simplified top view and a simplified side view, respectively, of the radiation pattern generated by the disinfection member in FIG. 10A.
Figure 14B:
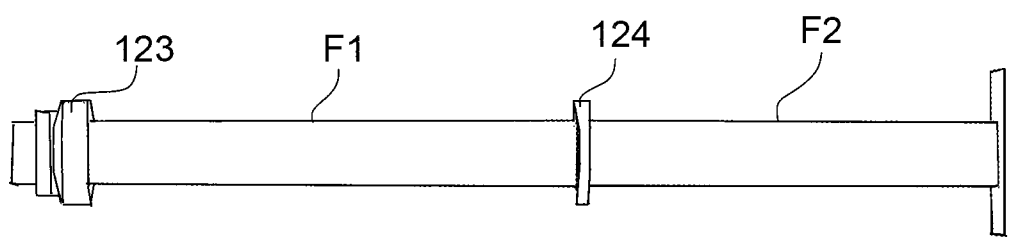
Figure 15:
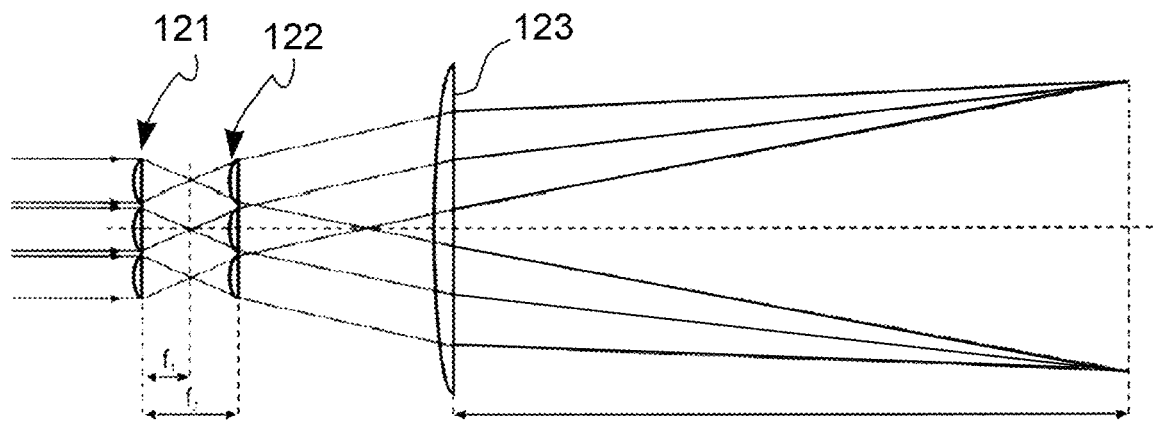
FIG. 15 shows a side view of the ray path of the radiation of a first detail of the optical assembly of the disinfection member in FIG. 10A.
Figure 16:
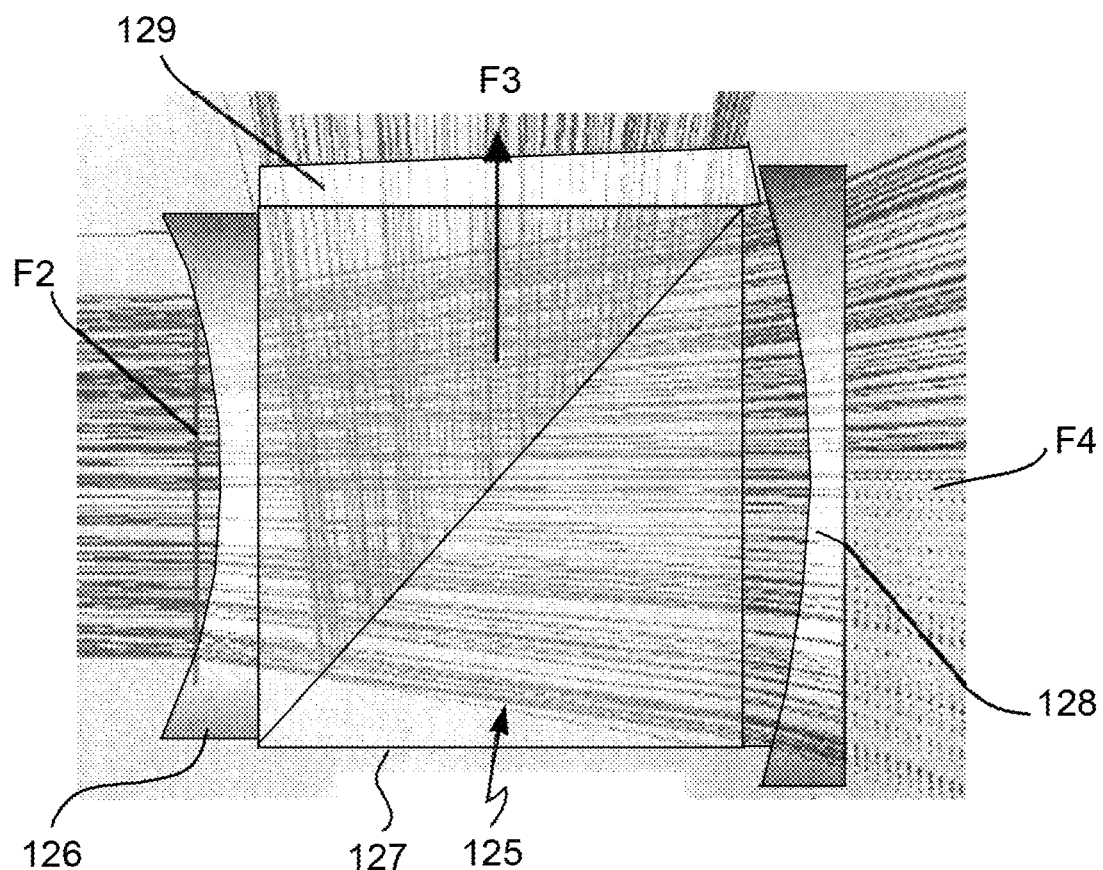
FIG. 16 shows a side view of a second detail of the optical assembly of the disinfection member in FIG. 10A.

In particular, the two cylindrical lenses (Fourier lenses) 123, 124 work on two transversal axes; first the various micro-beams generated by the two groups 121, 122 of micro-lenses are oriented in a square profile (lens 123) and then the outgoing beam is focused (lens 124), thus compressing one of the two dimensions and obtaining a section of beam F2 which is a thin rectangle (FIGS. 14A to 14B).

Thereby, by virtue of the employment of these two cylindrical lenses 123, 124 rather than an individual spherical lens, it is possible to have two different focal plans in the optical assembly 125, and therefore an improved concentration of the radiation in two well-collimated beams: one beam F4 directed towards the bottom of bottle C and one beam F3 directed towards the side walls of bottle C. When beam F2, collimated in the manner of a blade, reaches the optical assembly 125, the first concave cylindrical lens 126 ensures the beam remains collimated along the whole extension in the beam splitter 127, which as mentioned, has an internally tilted plane 127c, and thus, thanks to the collimation generated by the lens 126, it is simpler to make the optical wedge 129.

The part of beam F3 deflected towards the lateral direction impinges on the optical wedge 129. The object of the optical wedge 129 is to ensure the opening of the beam in vertical direction is such as to allow the lower edge of the bottle to be reached when the optical assembly 125 is close to the bottom of bottle C. The beam remains collimated in the horizontal direction by virtue of the action of the first concave cylindrical lens 126. Beam F4, which continues in longitudinal direction towards the bottom of the bottle, encounters the second concave cylindrical lens 128 which expands the beam in the manner of a fan to sweep the bottom in suitable manner by means of rotating stem 105, and therefore the optical assembly 125.

The optical assembly 125, with the beam splitter 127 in the middle with the two concave cylindrical lenses 126, 128 connected and the optical wedge 129, is contained in the end part of stem 105 by a hollow metal cylinder 130 (FIGS. 10A and 10C) comprising a first opening 130a at the longitudinal end of stem 109 and a second opening 130b on the side where the optical wedge 129 is arranged to allow the radiation beams F3, F4 to travel towards the wall and towards the bottom of bottle C, respectively.

The various optical assemblies are fastened both in stem 105 and in the end part as is common in optical technology for telescopes and optical assemblies with ordinary solutions.

Figure 13:
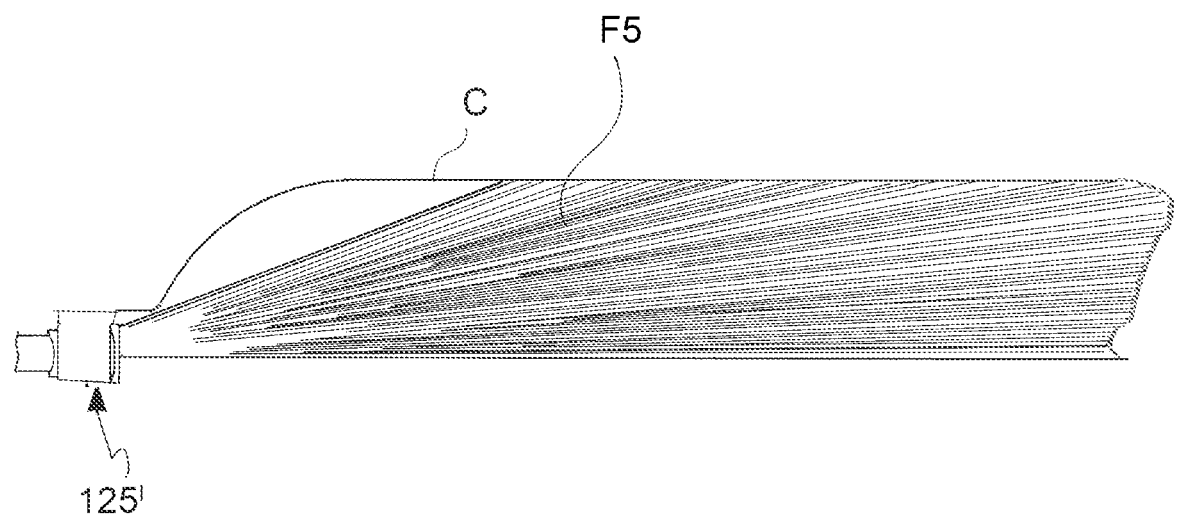
FIG. 13 shows the view in FIG. 12 in a different variant of the optical assembly.

According to a variant of the aforesaid embodiment shown in FIG. 13, instead of providing the optical assembly 125 to divide beam F2 into two other beams F3, F4 with two different directions, it is possible to provide an optical assembly 125' comprising gradient refractive index N (GRIN) lenses which bring beam F5 to take on the shape of a fan which is transversely thin but is longitudinally extended as much as the inside of the bottle is.

Figure 17:
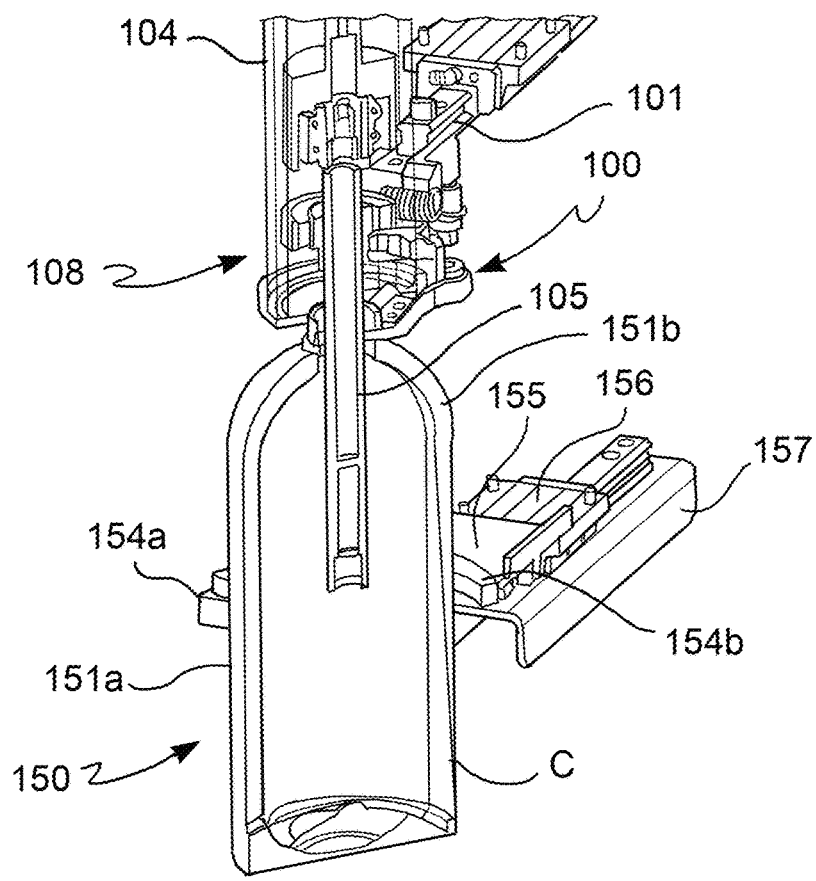
FIG. 17 shows a perspective view of a cut-away section of the disinfection member of the invention according to an embodiment.
Figure 18:
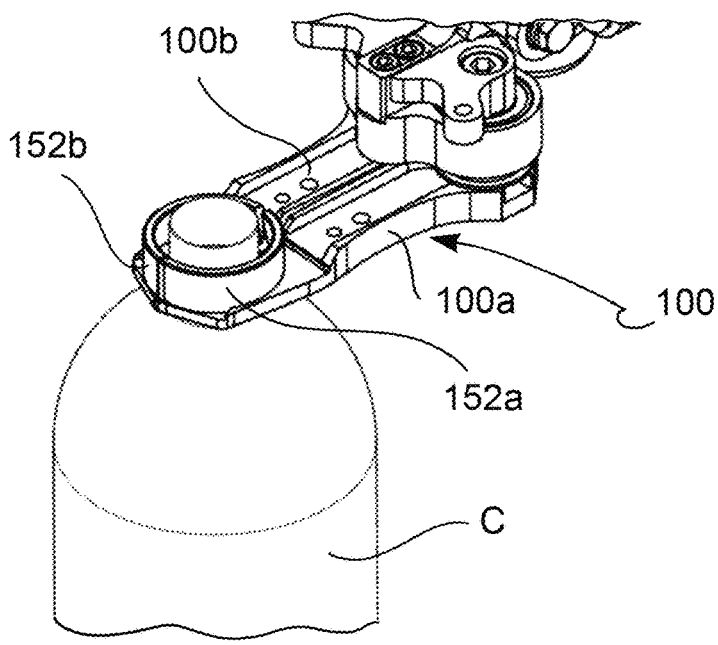
FIG. 18 shows a perspective view of a detail of the embodiment in FIG. 17.
Figure 19:
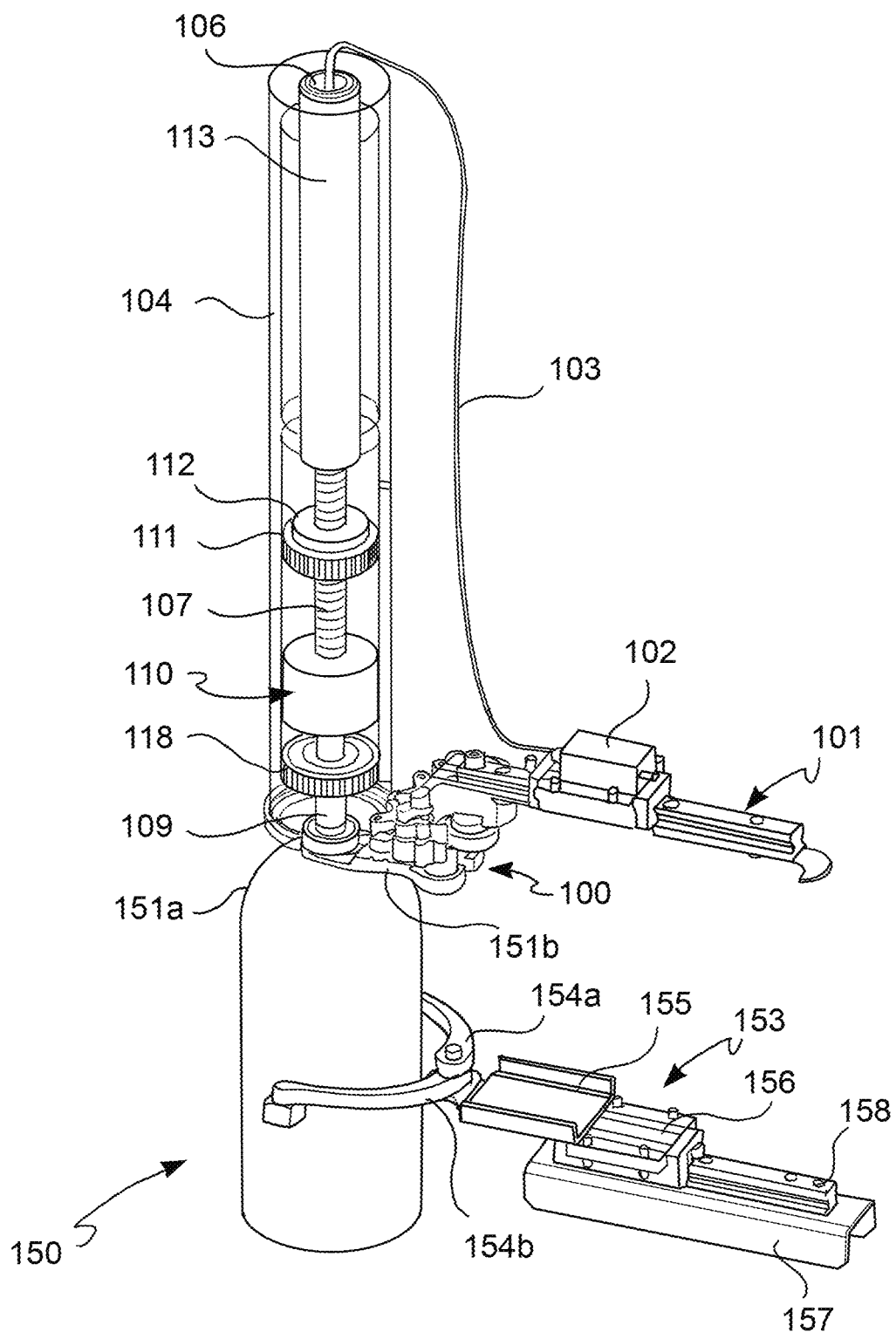
FIG. 19 shows a perspective view of a different detail of the embodiment in FIG. 17.

FIGS. 17 to 19 show an embodiment which uses the herein above-described disinfection member 108, but which additionally provides also irradiating the outer surface of bottle C by means of reflected radiation.

Indeed, for each of the possible solutions shown concerning the internal irradiation of the bottle, by acting on the wavelengths whereby the PET is transparent (non UV-C), the sterilizing beam crosses the walls of the bottle with a loss of intensity of less than 10%, and therefore an outer reflective structure, with the object of containing the electromagnetic radiation, which otherwise would be diffused in the body of the machine, allows the reflected radiation towards the surface of the bottle to be used for a sterilization of the outer surface thereof.

As shown in FIGS. 17 and 19, the disinfection member 108 comprises a receptacle 150 comprising two half-shells 151a, 151b configured to close about bottle C during the disinfection step, i.e. when stem 105 is introduced into the bottle and irradiates the inner surface thereof, as described above.

The inner surface of the half-shells 151a, 151b has a reflective covering, for example made by means of shiny metal plates, for example gold, aluminum, silver or chromium plates, or with dielectric/metal multilayers known in the field of optics.

The half-shells 151a, 151b are mounted on a mobile support 153 which is integral with the carousel of the disinfection unit 6. The half-shells 151a, 151b are integral with two nippers 154a, 154b supported on a plate 155 fastened to a slide 156 which is movable on a guide 158 between a retracted position and an extended position (shown in FIG. 19), wherein the half-shells 151a, 151b are arranged about bottle C. Guide 158 is in turn supported on an arm 157 fastened to the carousel.

The movement of the half-shells 151a, 151b may occur by means of cams arranged in suitable position on the carousel which actuate the movement into extended position and the closing prior to the beginning of the sterilization process, while other cams/abutments arranged on the carousel towards the end of the process select an abutment/cam connected with the two half-shells for opening prior to or during the release of the bottle.

When determining the shape, consideration must be made of the maximum size of the bottle to be contained, the reflection direction of the radiation beam so that the path it travels is no longer backwards in order to avoid reaching the laser source and damaging it, but simultaneously, since receptacle 150 has a substantially cylindrical symmetry, it reflects the beam towards the bottle while taking advantage of the effect of the convergence due to the cylindrical symmetry and, for this, the intensity of the radiation is nearly maintained.

The cylindrical and hemispherical shape of the inner surface of receptacle 150 indeed allows the thin shape, in the manner of a blade, of the laser beam to be concentrated, and therefore to be maintained with good approximation, here reflected towards the outer surface of the bottle. Thereby, a thin beam with high irradiance selectively acts on the micro-organisms and leaves the PET substrate unaltered. A further beneficial effect of the reflection of the electromagnetic radiation beam towards the body of the bottle lies in the fact that certain microbial forms may reside on the surface of the container or bottle, organized in several layers, thus resulting in the underlying layer being passively protected from the surface sanitizing actions. The available irradiance is capable of overcoming the protection given by the outer layers of micro-organisms. In any case, a simultaneous irradiating action on the opposite (outer) side results in a significant beneficial action.

As shown in FIG. 18, to allow the sanitization also of the neck of bottle C, gripper 100 comprises, at the end portion of the nippers 100a, 100b, i.e. the portion of gripper 100 which closes on the neck of the bottle, two reflective valves 152a, 152b capable of having the same effect also on the outer surface of the neck.

Although it is not in contact with the product, the sanitization of the outer part of the bottle however can be appreciated because it ensures the filling process in the filling machine has greater sanitization.

In general, the neck and the bottom are the parts which require a more intense internal sterilization because they suffered less from the thermal action of the heating oven of the preforms.

It is apparent that only certain particular embodiments of the present invention have been described, to which those skilled in the art can make all those modifications required for adapting it to particular applications, without moreover departing from the scope of protection of the present invention.

What We claim is:

1. A disinfection unit of containers or preforms, comprising a carousel on which there is supported a plurality of disinfection members which are movable between a raised position and a lowered position, wherein said lowered position is configured so as to allow the disinfection members to be introduced into said containers or preforms to be disinfected, wherein each of said disinfection members comprises a plurality of disinfection elements emitting UV-C radiation or is connected with a laser source which emits UV-C or visible-infrared radiation (VIR), wherein the disinfection member comprises a stem which is vertically movable between a raised position, in which the stem is positioned above the neck of the bottle, and a lowered position, in which a lower portion of the stem is inserted in the bottle, wherein the stem comprises:
   an upper portion having tubular shape, so as to incorporate therein an optical path of the laser radiation conducted by an optical fiber, the upper portion having a feed-screw outer surface,
   a rotatable lower portion, configured so as to insert into the neck of the bottle, and
   a bushing or bearing element which is integral with the upper portion and wherein the lower portion is rotatably associated.

2. The disinfection unit according to claim 1, comprising a containment structure in which a controlled atmosphere is maintained by means of an overpressure of sterile air.

3. The disinfection unit according to claim 2, comprising ventilation means, downstream of which a dehumidification device and a sterile filter are arranged so as to introduce dry and sterile air, pre-cooled sterile dry air, into the containment structure.

4. The disinfection unit according to claim 1, wherein:
   the disinfection elements are UV-C radiation LEDs, characterized by a narrow emission spectrum in the 200-290 nm range, with peak wavelengths of 265 nm and/or 275 nm, or
   the laser source emits UV-C radiation in the range of 250 to 330 nm or visible-infrared radiation (VIR) in the range of 400 to 1200 nm.

5. The disinfection unit according to claim 1, wherein the stem is contained in a casing and comprises a first actuator, fastened to the inner wall of the casing in substantially median position, configured so as to put into rotation a guide element including a recirculating-ball guide, a screw or a helical guide made of self-lubricating material, which guide element applies a torque to the feed-screw surface of the upper portion, and wherein the upper portion is fastened in rotation so that the upper portion of the stem may only take on a vertical translational motion under the action of the torque applied by the first actuator, by virtue of the feed-screw profile which interacts with the rotating guide element.

6. The disinfection unit according to claim 5, wherein the upper portion of the stem is accommodated in a tubular element comprising vertical grooves, there being arranged, at the upper end of the upper portion, shoes which are inserted into said vertical grooves so that the rotation of the upper portion is prevented.

7. The disinfection unit according to claim 1, wherein a second actuator is positioned at the lower portion of the stem and incorporates, in the rotor thereof, the stem itself, so that the rotary action is transmitted to the lower portion of the stem which is therefore free to slide vertically integrally with the translational motion of the upper portion and to rotate integrally with the rotor of the second actuator.

8. The disinfection unit according to claim 1, wherein the stem encloses therein an optical system which defines the optical path of the radiation generated by the laser source, said optical system comprising, in order:
- a collimator;
- a first and a second group of cylindrical micro-lenses;
- a first and a second cylindrical lens;
- an optical assembly comprising, in order: i) a first concave cylindrical lens, ii) a beam splitter, iii) a second concave cylindrical lens and iv) an optical wedge arranged at the beam splitter, perpendicularly with respect to the first and second concave cylindrical lens.

9. The disinfection unit according to claim 8, wherein the beam splitter is formed by two prisms joined along a plane tilted by 45°, wherein the two faces of the prisms comprise a coating which allows dividing the radiation into a first beam with transverse direction through the optical wedge, directed towards the wall of the bottle, and into a second beam with longitudinal direction, directed towards the bottom of the bottle, wherein said coating is a layer consisting of a photonic crystal which, through an electrical or magnetic signal, allows the related intensity of the two divisions of the two radiation beams to be selected during the disinfection process.

10. The disinfection unit according to claim 1, wherein the disinfection member comprises a receptacle comprising two half-shells configured to close about the bottle during the disinfection step when the stem is introduced into the bottle and irradiates the inner surface thereof, the inner surface of the half-shells having a reflective coating.

11. The disinfection unit according to claim 10, comprising a gripper for supporting the bottle below the disinfection member, wherein said gripper comprises two reflective valves configured to reflect the radiation emitted by the stem onto the outer wall of the neck of the bottle.

12. A blowing and filling system of containers, comprising a heating oven for preforms inlet into the system by means of handling means, a blowing or stretch-blowing unit placed downstream of the oven, and a filling unit with a filling product, arranged downstream of the blowing unit, said system comprising a disinfection unit according to claim 1, wherein said disinfection unit is arranged:
- upstream of the oven for the sterilization of the preforms, or
- downstream of the blowing or stretch-blowing unit for the sterilization of the containers.

* * * * *